United States Patent
Greenhut et al.

[11] Patent Number: 5,683,426
[45] Date of Patent: Nov. 4, 1997

[54] APPARATUS AND METHOD FOR DETECTING THE PROGRESSION OF AV NODAL BLOCK AND ATRIAL CAPTURE

[75] Inventors: Saul E. Greenhut, Aurora; Richard Lu, Highlands Ranch, both of Colo.

[73] Assignee: Pacesetter, Inc., Sylmar, Calif.

[21] Appl. No.: 705,339

[22] Filed: Aug. 29, 1996

[51] Int. Cl.$^6$ ............................................. A61N 1/362
[52] U.S. Cl. .............................................................. 607/9
[58] Field of Search ............................................ 607/9, 25

[56] References Cited

U.S. PATENT DOCUMENTS

| | | |
|---|---|---|
| 5,144,950 | 9/1992 | Stoop et al. |
| 5,174,289 | 12/1992 | Cohen ............... 607/9 |
| 5,318,594 | 6/1994 | Limousin et al. ....... 607/9 |
| 5,441,523 | 8/1995 | Nappholz . |
| 5,514,163 | 5/1996 | Merkowitz et al. ....... 607/9 |

*Primary Examiner*—William E. Kamm
*Assistant Examiner*—George R. Evanisko
*Attorney, Agent, or Firm*—Gottlieb, Rackman & Reisman

[57] ABSTRACT

A pacemaker operating in an AAI or AAIR mode is provided with a detector for monitoring an atrial lead and detecting cross talk or far field R-waves from the ventricle. This signal is used to detect and monitor AV nodal block and its progression in a patient. The same signal may also be used to indicate atrial capture.

16 Claims, 6 Drawing Sheets

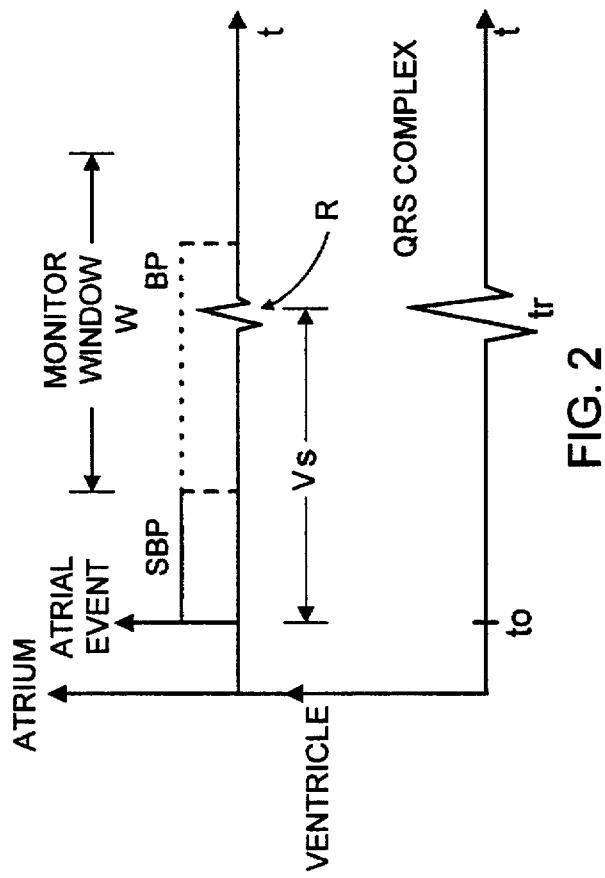
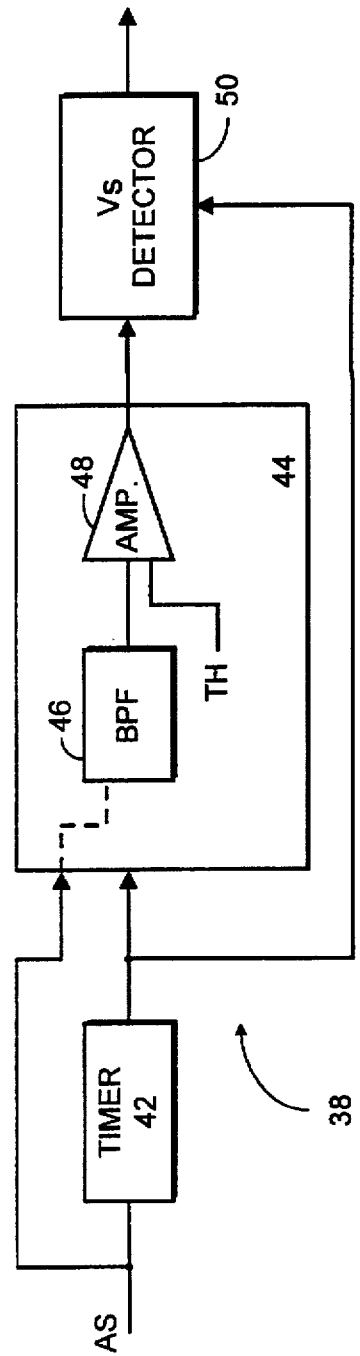
FIG. 2
FIG. 3

APPARATUS AND METHOD FOR DETECTING THE PROGRESSION OF AV NODAL BLOCK AND ATRIAL CAPTURE

BACKGROUND OF THE INVENTION

A. Field of Invention

The present invention pertains to an apparatus, such as a pacemaker, for detecting a far field R-wave in an atrial lead coupled to the pacemaker. The R-wave may be used for a number of different purposes, depending on the condition of the patient. First, the R-wave may be used to detect the occurrence and progression of AV nodal block in a patient. If AV nodal block is detected, its progression is monitored to determine when such a condition requires additional therapeutic steps. If the clinician confirms that AV nodal block is not present, the R-wave may be used to detect and confirm atrial capture.

B. Description of the Prior Art

Patients suffering from sick sinus syndrome with intact A-V conduction in the heart may be provided with an atrial synchronous (AAI or AAIR) mode, pacemaker hereinafter referred to as AAIX mode, or a dual chamber programmable pacemaker operating in an AAIX mode. However, some of these patients develop AV nodal block after implantation. Patients provided with single chamber pacemakers can be helped if their pacemaker is upgraded to dual-chamber. Patients provided with dual chamber pacemakers can be helped if their pacemaker is switched to a dual chamber mode. Obviously these procedures are most effective if the AV nodal block is detected as early as possible. However, until now, no implantable pacemaker has been provided with a means of automatically detecting AV nodal block when in AAIX mode and indicating this condition to the attending clinician.

OBJECTIVES AND ADVANTAGES OF THE PRESENT INVENTION

In view of the above-mentioned disadvantages of the prior art, it is an objective of the present invention to provide a pacemaker with a means of detecting an AV nodal block (including a 1°, 2° (including Mobitz I and Mobitz II), 3° block or any combination thereof) in a patient, using a standard implantable cardiac device.

A further objective is to provide a method and apparatus for detecting an AV nodal block by monitoring signal activity sensed on an atrial lead, such as the far field R-wave.

Yet another objective is to provide a method and apparatus for determining other cardiac activity from the atrial lead, such as atrial capture.

Other objectives and advantages of the invention shall become apparent from the following description. Briefly, a pacemaker constructed in accordance with this invention includes means for monitoring electrical cardiac activity in at least one of the chambers of the patient's heart. More specifically, means are provided for defining a monitoring window of a predetermined duration, and initiated a predetermined time after an atrial event, such as an intrinsic atrial beat, or an atrial sense or pacing pulse. During this time the preselected chamber (preferably the atrium) is monitored automatically preferably by the pacemaker to detect a far-field R-wave associated with the atrial event. Absence or delayed presence of this R-wave is indicative of a potential AV nodal block. Both the occurrence of the R-wave and its absence are logged in the pacemaker and downloaded to a programmer for analysis by the attending physician. The far field R-wave may also be used to provide other indication, such as for example atrial capture. Alternatively or additionally, the far-field R-wave may be monitored by the programmer.

BRIEF DESCRIPTION OF THE DRAWINGS

FIG. 2 shows the events taking place in the atrium and ventricle during a typical cardiac cycle;

FIG. 3 shows a schematic diagram for an AV nodal block determinator for the pacemaker of FIG. 1;

DETAILED DESCRIPTION OF THE INVENTION

In the following discussion, a dual chamber pacemaker is disclosed, it being understood that at least initially, the pacemaker is programmed for an AAIX mode in which ventricular activity from a ventricular lead is ignored. The present invention is also applicable to single chamber pacemakers.

Figure 1:
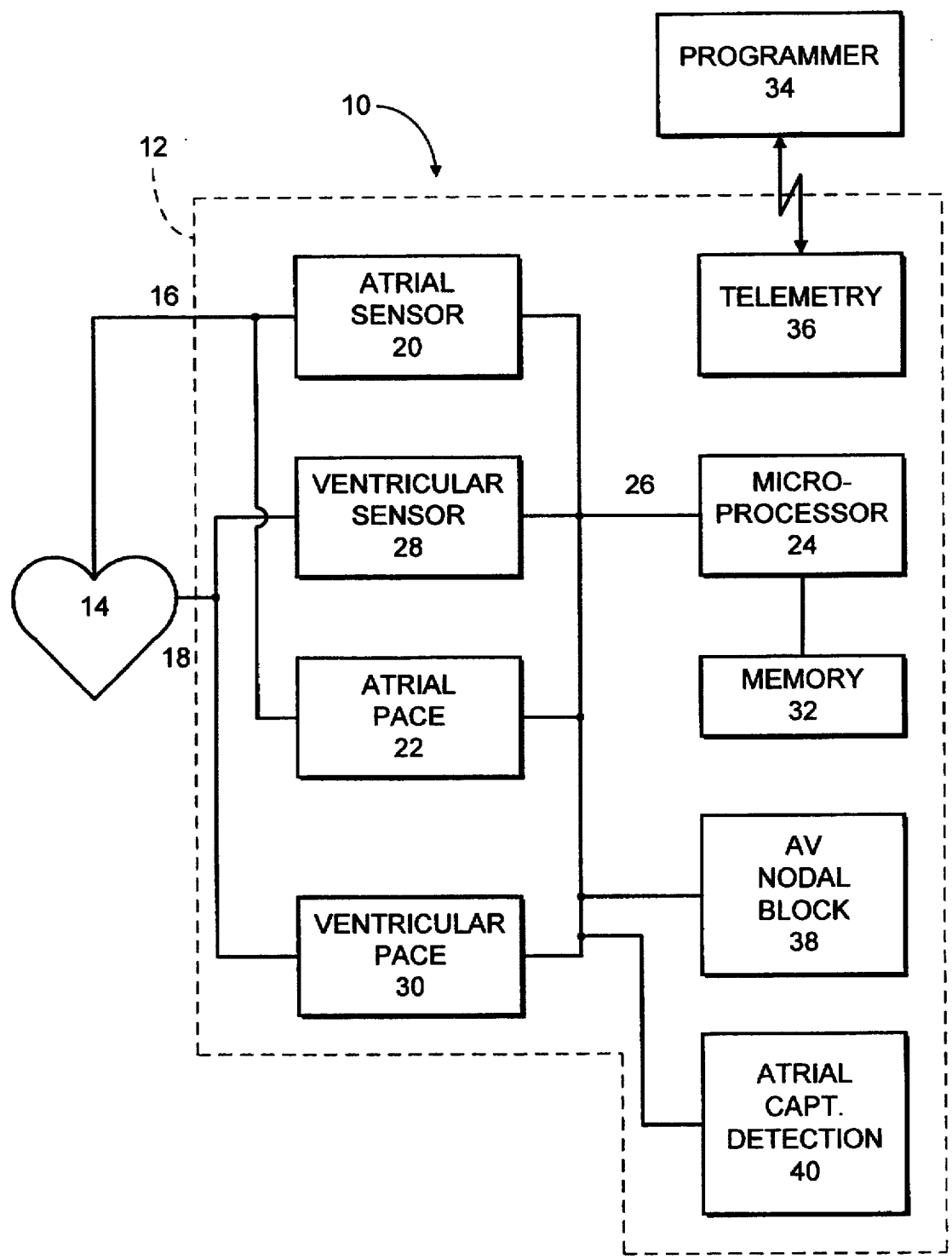
FIG. 1 shows a block diagram of a pacemaker constructed in accordance with this invention.

Referring now to FIG. 1, an implantable pacemaker 10 constructed in accordance with this invention includes a hermetic housing 12. The pacemaker 10 communicates with the atrium of a heart 14 by electrode 16. A second electrode 18 may be provided for communication with the ventricle as a safety measure, however such an electrode is not necessary for an AAIX mode. Electrodes may be unipolar or bipolar, or may have any other configuration. Briefly, the electrode 16 is connected to an atrial sensor 20 and an atrial pacer 22. The atrial sensor 20 senses electrical signals from the atrium via electrode 16 and generates corresponding signals which are transmitted to a microprocessor via a bus 26. The microprocessor 24 monitors atrial activity and, if necessary, sends commands on bus 26 to atrial pacer 22 requesting that atrial pacing pulses be transmitted via electrode 16.

Similarly, if provided, electrode 18 is connected to a ventricular sensor 28 and ventricular pacer 30. These circuits 28, 30 also communicate with the microprocessor 24 via bus 26.

Programming and data for the microprocessor 24 are stored in a memory 32. This data can be downloaded and the microprocessor programming can be upgraded by establishing communication with an external programmer 34 through a telemetry circuit 36.

A more detailed description of the features of pacemaker 10 described so far and its elements are found in U.S. Pat. No. 5,441,523, incorporated herein by reference.

Importantly, the pacemaker 10 further includes an AV nodal block detector 38 and optionally an atrial capture detector 40. The purpose of the detector 38 is to monitor AV nodal block in a patient, as well as its progression. The nodal block (if any) and its progression are stored by the microprocessor 24 into memory 32. The patient is normally requested to return to a physician for normal check ups. As part of this procedure, the AV nodal block condition can be retrieved or downloaded from memory 32 into programmer 34 and displayed to the physician. If this condition has sufficiently deteriorated or the progression indicates a rapid decline, the physician may decide to take corrective measures, such as, for example, switching pacemaker 10 from an AAIX to DDDX mode.

More specifically, in FIG. 2 typical cardiac activity is illustrated, with the top trace showing the activity in the atrium and the bottom trace showing the activity in the ventricle as a function of time. Specifically, at t=t0 an atrial event AE occurs which may be an intrinsic wave as or, in the absence of such a wave, an atrial pacing pulse may be applied. In a patient with normal A-V nodal conduction after a duration usually referred to as the PR interval, the atrial event produces a QRS complex in the ventricle, as indicated on the bottom trace of FIG. 2. This QRS complex also results (at t=tr) in a small signal R in the atrium normally referred to as the far-field R-wave. Following the atrial activity, in prior art pacemakers, typically a blanking period BP was imposed in order to suppress any noise or crosstalk from the ventricle. This blanking period BP was set normally to exceed the expected PR interval as indicated in FIG. 2 by the dotted lines. One of the purposes of the blanking period BP is to suppress the far-field R-wave so that this later wave is not mis-interpreted by the atrial sensor 20 as an intrinsic P wave.

However, in the present invention, instead of the long blanking period BP, a much shorter period SBP of about 80 msec is provided. The purpose of SBP is to prevent sensing the atrial event if an atrial pace and prevent sensing the atrial event more than once if an atrial sense. This short blanking period SBP is followed by a monitor window W. During this window, the atrial detected, the period Vs between t0 and tr is measured and logged, together, optionally, with morphological characteristics of the signal R. If the signal R is not detected, 2° or 3° AV nodal block is indicated.

As a patient develops AV block over time, the period Vs may increase and/or the QRS signal may be completely blocked. Therefore, the duration Vs can be used as an index of the AV nodal block and its progression. Typically in a patient with no nodal AV block, Vs is in the range of about 150 ms. As nodal AV block sets in, Vs may increase or the QRS signal may intermittently be blocked. A patient with PR interval (Vs) greater than approximately 200 ms may benefit from dual chamber pacing. Therefore, for patients exceeding this limit, or patients exhibiting limited or no far field R-wave activity (2° or 3° block) following an atrial event, the use of additional cardiac assistance should be investigated (i.e., dual chamber pacing).

Details of a preferred embodiment for detecting a far-field R-wave are shown in FIG. 3. The output As of the atrial sensor 20 is fed to timer 42 and an R-wave detector 44. The timer 42 defines the window W during which the atrial sensor output is monitored for R-waves and it enables the R-wave sensor 44. The R-wave may be sensed using various methods. In one method the sensor 44 may consists of a band pass filter 46 for filtering the output of the sensor 20. The output of the filter 46 is then fed to an amplifier 48 which compares the output of the filter 46 to a threshold level TH. The outputs of amplifier 48 and the timer 42 are fed to a detector 50. The interval between the onset of window W as set by timer 42 and the detection of a far-field R-wave is the parameter Vs and is determined by the detector 50.

The duration of window W and the threshold TH may be preset or may be programmable variables. For this latter implementation, the detector 38 may be implemented in microprocessor 36. Normally the atrial sensor 20 includes a band pass filter for filtering the atrial event signals (As, Ap). Band pass filter 46 may be implemented in the atrial sensor and provide both functions. Alternatively, a separate band pass filter may be provided for the R-wave detector 38 as shown in FIG. 3. In this latter implementation, the band pass filter may have lower frequency characteristics than the band pass filter of the atrial sensor.

Figure 4:
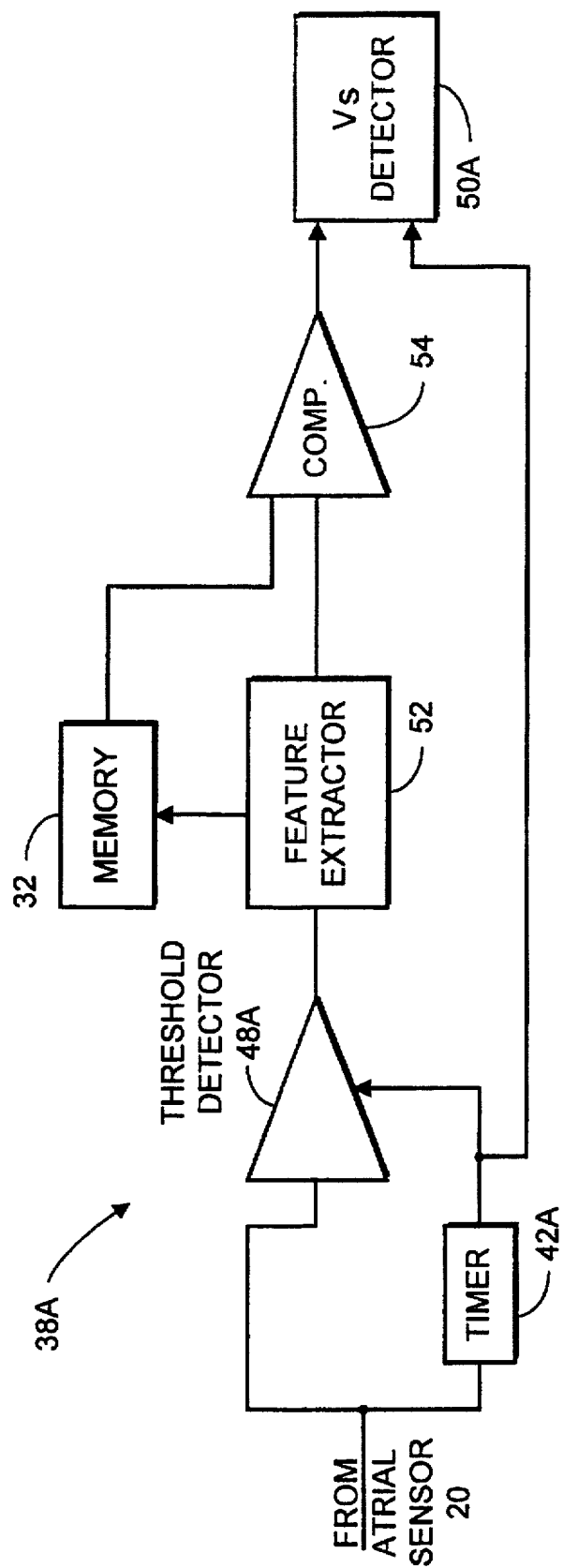
FIG. 4 shows an alternate embodiment for an AV block determinator.

Another far-field R-wave detector 38A is shown in FIG. 4. In this Figure, the signal from sensor 20 is fed to timer 42A and a threshold detector 48A. The timer 42A sets the window W, as discussed above to enable the detector 48A. The output of the detector 48A is fed to a feature extractor 52 which extracts certain morphological features from the R-wave. These features distinguish a far-field R-wave from other signals detected by sensor 20, such as electromagnetic radiation or atrial repolarization and may include duration, peak amplitude, polarity, integral, and so on, as well as a combination of these features. The memory 32 is used in this case also to store known characteristics of far field R-waves. These known characteristics are compared to the features extracted by extractor 52 by comparator 54. If a match is found, the comparator 54 generates a signal indicative of a far-field R-wave. Alternatively the feature extractor may generate a waveshape for the received signal and this waveshape maybe compared by comparator 54 to a far field R-wave template received from memory 32. The output of comparators 54 and timer 42A are fed to a Vs detector for generating the parameter Vs as defined above.

The Vs detector 50, 50A sends the value of each interval or parameter Vs determined during a particular cardiac cycle to memory 32 (FIG. 1). The characteristics of the far-field R-wave from the R-wave detector 38A may also be stored into the memory 32. If at the end of window W the R-wave detector fails to detect an R-wave this event is also stored in memory 32. Vs is set to a special value (e.g., W+1) to indicate a 2° or 3° AV block event.

Thus, between visits to the doctor by the patient, the memory 32 accumulates a profile for the Vs parameter and counts the number of times and the sequence during which no R-wave has been detected. The memory 32 may also accumulate a profile of the R-wave characteristics. Other information may also be stored in the memory 32 and downloaded to indicate if each atrial event was intrinsic or paced, the peak amplitude of the sensed atrial events, and other similar information which may assist the clinician in making a diagnosis. At the next clinic visit, the information collected in memory 32 is downloaded into programmer 34 and displayed. This information provides indication to the clinician as to the extent (if any) and progressive deterioration of the AV nodal block.

Figure 5A:
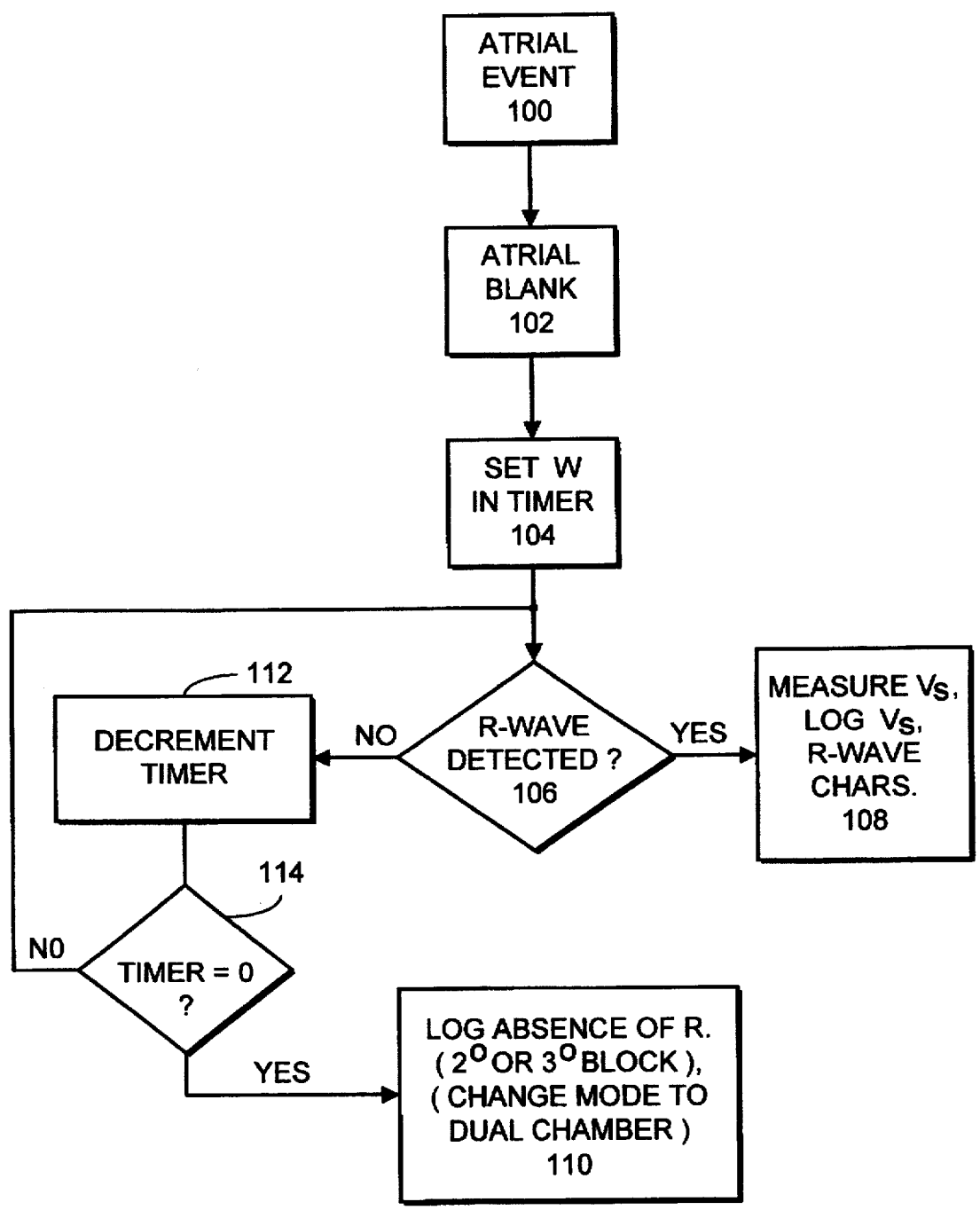
FIGS. 5A, B, and C show alternative flow charts for the operation of the pacemaker.

One operation of the detector 38 is described in conjunction with the flow chart of FIG. 5A and FIG. 2. In step 100 an atrial event occurs. In step 102, a short blanking period (SBP) is set. In step 104 a monitoring window W is set in timer 42. During this window W, the atrial sense signal is monitored for a far field R-wave. If an R-wave is detected within the window W by step 106 then in step 108 the parameter Vs and possibly other characteristics of the R-wave are determined and logged as described above.

If no R-wave is detected in step 106, then in step 110 the timer is decremented. In step 112 if the timer 42 has not reached zero, then step 106 is repeated. Otherwise, in step 114, this event is logged as a special value for Vs, to indicate that either a 2° or 3° A-V block has occurred, or that the atrial pacing pulse has failed to capture the atrium.

If at times a long Vs is measured or no R-wave is detected in W, the clinician may elect to reprogram the pacemaker from a single to a dual chamber mode. Alternatively, the microprocessor could be programmed to check the Vs parameter periodically, as well as the number of times N that an R-wave was not detected. If Vs or N exceed a certain threshold then the microprocessor may automatically switch to a dual chamber mode.

Detection of atrial capture is a difficult problem for state-of-the-art pacemakers. In the present invention, provisions are made to differentiate lack of atrial capture from an A-V block, using the far field R-wave.

Figure 5B:
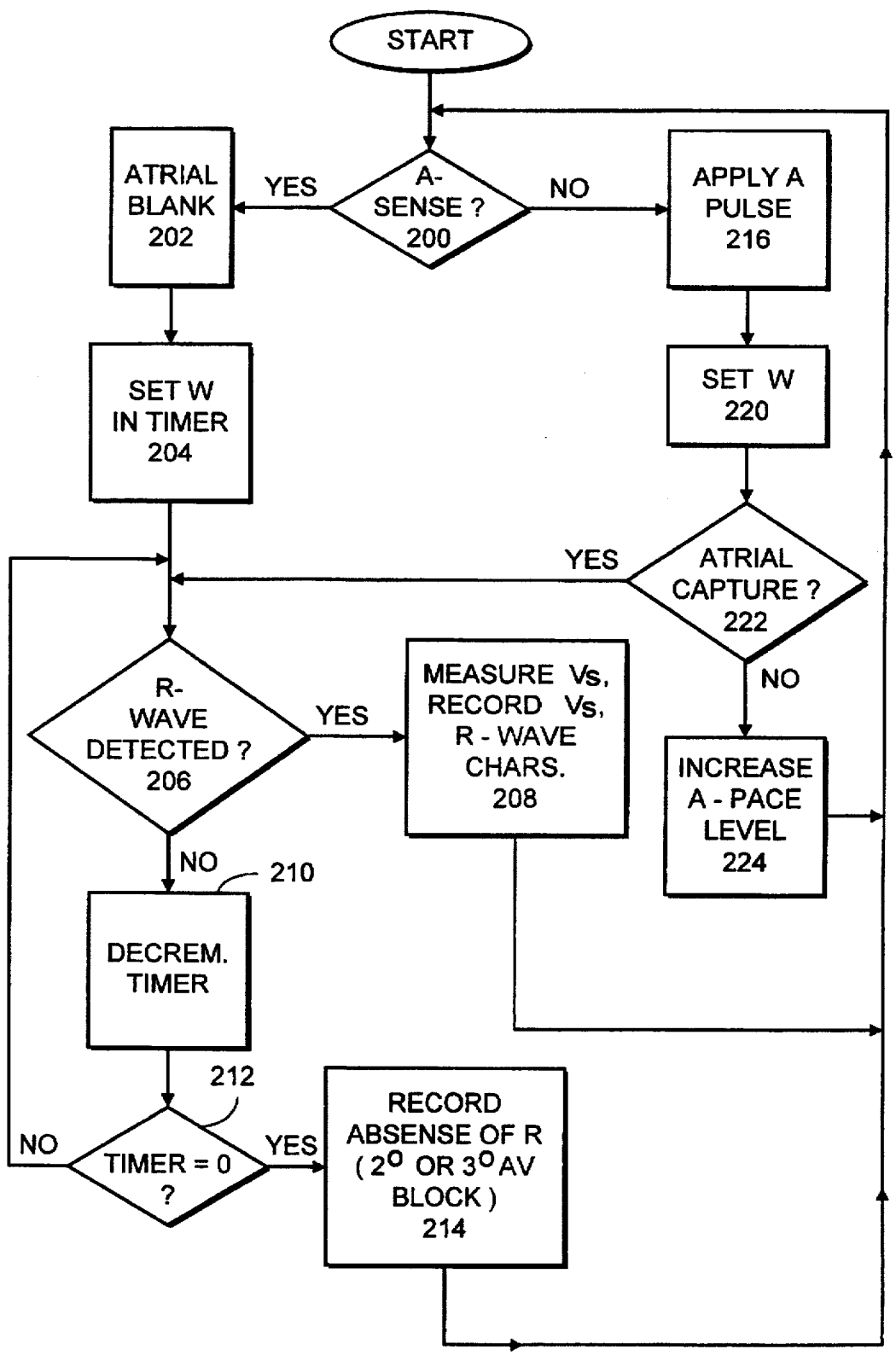
Figure 5C:
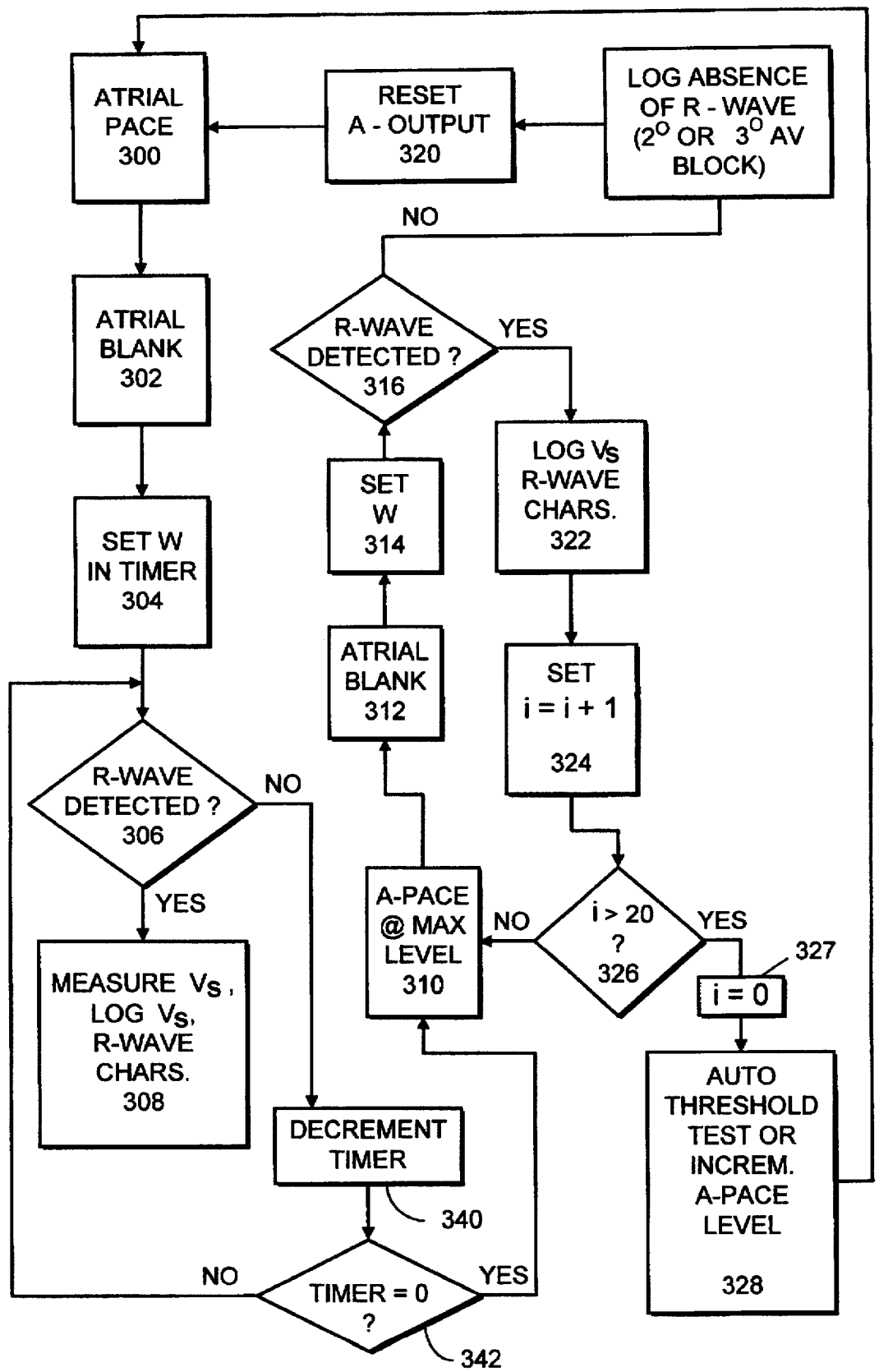

Two such modes of operation are shown in FIGS. 5B and 5C. FIG. 5B uses the atrial paced depolarization while FIG. 5C uses the ventricular far-field depolarization to detect atrial loss of capture.

One mode of operation is shown in FIG. 5B. In this mode, in step 200 a predetermined period is set for sensing an intrinsic atrial depolarization. If this atrial depolarization is sensed (A-sense) then in step 202, the atrium is blanked for a short period (SBP). In step 204 window W is set in the timer 42 at the end of the blanking period. If during window W an R-wave is detected (step 206) then its parameter(s) (i.e. Vs, and other characteristics) are stored in step 208. If no R-wave is sensed then in step 210, timer 42 is decremented. In step 212, if the timer 42 has not reached zero, the search for the R-wave in window W continues. Otherwise, in step 214 a 2° or 3° block is logged. The operation set forth so far is very similar to the operation described in FIG. 5A. However, in this embodiment, if in step 200 an intrinsic atrial pulse is not sensed, then in step 216 an atrial pacing pulse is applied. In step 220 window W is set, and in step 222 a test is performed to determined if the pacing pulse of step 216 has captured the atrium. This step may be performed for example, by using techniques disclosed in U.S. Pat. No, 4,858,610, incorporated hereinby reference. If capture is detected, then the AV block determination is continued in step 206.

If it is determined that the atrium is not captured by the pacing pulse (step 222) then the atrial pacing level (pulse amplitude and/or duration) is increased in step 224, and the process is repeated in the next atrial cycle. If the atrium is captured by the pacing pulse (step 222) usual A-V block determination continues in step 206.

Another embodiment is shown in FIG. 5C. In this embodiment steps 300-308 are similar to steps 100-108 in FIG. 5A. The difference is in the way missing R-waves are handled. In step 306 if an R-wave is not detected, the counter is decremented in step 340. In step 342, the counter is checked to see if it reached zero. If not, the test is continued. If yes, then the reason for this missing R-wave may be because either the atrium has not been captured or AV block has occurred. Therefore in step 310 an atrial pacing pulse (A-pace) is issued at a proper time and a maximum output. In step 312 an atrial blanking signal is provided. In step 314 a window W is set. In step 316 a determination is made as to whether an R-wave is detected in window W. If an R-wave is detected then the parameter Vs and the R-wave parameters are logged in step 322. In step 324 a parameter i is incremented. In step 326 if the parameter i is less than a preset number, such as 20, then atrial pacing at maximum amplitude is continued in step 310. In step 316 if an R-wave is not detected, even at the maximum atrial pacing pulse amplitude set in step 310, then 2° or 3° AV block failure is assumed. In step 318 this AV conduction failure is logged. Optionally, the mode is also automatically changed to dual-chamber. In step 320 the atrial pacing output is reset to its programmed value and normal atrial pacing is continued in step 300.

In step 326 if the atrium is captured more than 20 times consecutively at the high amplitude without 2° or 3° AV block, then in step 327 i is reset and in step 328 an automatic atrial pacing threshold test is made as described in U.S. Pat. No. 4,858,610 incorporated herein by reference. Alternatively, the atrial pacing level is automatically increased in step 328 without performing a threshold test. Normal pacing is then continued (step 300).

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

We claim:

1. An implantable pacemaker comprising:

atrial sensor means for sensing atrial activity in a patient's atrium and generating corresponding atrial sense signals, said atrial activity including an intrinsic atrial beat and a ventricular event;

pacing means for generating an atrial pacing pulse;

control means for receiving and analyzing said atrial sense signals and for controlling said pacing means responsive to said atrial sense signals; and AV nodal block sensing means receiving said atrial sense signals for sensing an AV nodal block of said heart, said AV nodal block sensing means generating an AV block indication signal based on an atrial event and said ventricular event, said atrial event being defined by one of said intrinsic atrial beat and said atrial pacing pulse.

2. The pacemaker of claim 1 wherein said AV nodal block sensing means includes timing means for defining a monitor window following said atrial event, said ventricular event being sensed during said monitor window.

3. The pacemaker of claim 1 wherein said atrial sensor means includes a detector for detecting a far field R-wave.

4. An implantable pacemaker comprising:

an atrial electrode extending into an atrium of a patient's heart;

an atrial sensor for sensing an atrial event including an intrinsic atrial beat on said electrode for generating atrial signals;

an atrial pacer for generating atrial pace pulses for said atrium in response to pacing commands;

a controller for generating said pacing commands, said pacing commands being generated if said intrinsic atrial beat is not sensed by said atrial sensor in a preselected period;

a ventricular sensor for generating a ventricular sense signal indicative of a ventricular event on said atrial electrode in said atrium, said ventricular sensor being coupled to said electrode; and a detector generating a parameter indicative of AV nodal block in the patient based on an atrial event and ventricular sense signal, said atrial event comprising one of said atrial pace pulses and an intrinsic atrial beat.

5. The pacemaker of claim 4 wherein said detector measures time duration between said atrial event and said ventricular event and detects absence of a ventricular event.

6. The pacemaker of claim 5 further comprising storage means for storing said parameter.

7. The pacemaker of claim 4 wherein said detector monitors a far field R-wave in said electrode.

8. The pacemaker of claim 7 wherein said detector extracts wave shape characteristics of said far field R-wave.

9. The pacemaker of claim 4 further comprising capture indication means for indicating atrial capture, based on said ventricular event.

10. The pacemaker of claim 9 further comprising means for increasing said atrial pacing pulses when said capture indication means indicates a loss of atrial capture.

11. The pacemaker of claim 4 further comprising memory means for storing signals indicative of said block.

12. A dual chamber pacemaker comprising:

programmable means operable in an atrial/operating mode wherein only an atrium of a patient's heart is paced and a dual chamber operating mode wherein said atrium and a ventricle of the patient's heart is paced; and detector means receiving cardiac atrial and ventricular activity only through said atrium for detecting an AV block condition of said patient;

wherein said programmable means switches from said atrial operating mode to said dual chamber operating mode in response to said AV block condition.

13. The pacemaker of claim 12 wherein said detector means is arranged and constructed to detect far-field R waves.

14. The pacemaker of claim 13 wherein said detector means includes means for setting a monitoring window and atrial sensing means for detecting said far-field R-wave during said window.

15. The pacemaker of claim 14 wherein said atrial sensing means includes means for measuring pre-determined characteristics of signals sensed in said window and means for comparing said characteristics to stored values.

16. The pacemaker of claim 13 further comprising capture detection means for detecting capture, said capture detecting means being responsive to the detection of said far-field R-waves.

* * * * *